United States Patent [19]

Sheu et al.

[11] Patent Number: 5,700,559
[45] Date of Patent: Dec. 23, 1997

[54] DURABLE HYDROPHILIC SURFACE COATINGS

[75] Inventors: Min-Shyan Sheu, Lowell; Ih-Houng Loh, Lexington, both of Mass.

[73] Assignee: Advanced Surface Technology, Billerica, Mass.

[21] Appl. No.: 357,415

[22] Filed: Dec. 16, 1994

[51] Int. Cl.$^6$ ........................................... B32B 5/22
[52] U.S. Cl. ........................... 428/319.7; 428/319.9; 428/407; 428/420
[58] Field of Search ................... 428/319.7, 319.9, 428/407, 420

[56] References Cited

U.S. PATENT DOCUMENTS

| | | | |
|---|---|---|---|
| 4,168,112 | 9/1979 | Ellis et al. | 351/160 H |
| 4,312,575 | 1/1982 | Peyman et al. | 351/160 H |
| 4,436,730 | 3/1984 | Ellis et al. | 424/180 |
| 4,613,665 | 9/1986 | Larm | 536/20 |
| 4,921,497 | 5/1990 | Sulc et al. | 623/6 |
| 4,980,208 | 12/1990 | Sugiyama et al. | 427/444 |
| 5,039,421 | 8/1991 | Linder et al. | 210/651 |
| 5,049,282 | 9/1991 | Linder et al. | 210/651 |
| 5,118,537 | 6/1992 | Sugiyama et al. | 427/444 |
| 5,120,440 | 6/1992 | Nemoto et al. | 210/490 |
| 5,132,108 | 7/1992 | Narayanan et al. | 424/78.17 |
| 5,137,633 | 8/1992 | Wang | 210/490 |
| 5,208,111 | 5/1993 | Decher et al. | 428/420 |
| 5,380,303 | 1/1995 | Holly et al. | 604/290 |

FOREIGN PATENT DOCUMENTS 0 294 905 A1  12/1988  European Pat. Off. .

OTHER PUBLICATIONS

BASF Product Catalog, "For Your Unlimited Imagination: Polymin (Polyethylenimine) From BASF Corporation", 1992.

Golander et al., *J. Colloid and Interface Science*, 119(1):38–48 (1987), "ESCA Studies of the Adsorption of Polyethyleneimine and Glutaraldehyde Reacted Polyethyleneimine on Polyethylene and Mica Surfaces".

Koziol et al., *Arch Ophthamol*, 101:1779–1781 (1983), "Evaluation of a New Silicone–Methane Polymer Contact Lens".

*Primary Examiner*—D. S. Nakarani
*Attorney, Agent, or Firm*—Fish & Richardson P.C.

[57] ABSTRACT

A hydrophilic article for use in aqueous environments, including a substrate, an ionic polymeric layer on said substrate, and a disordered polyelectrolyte coating ionically bonded to said polymeric layer.

14 Claims, No Drawings

DURABLE HYDROPHILIC SURFACE COATINGS

BACKGROUND OF THE INVENTION

Several methods are available to improve the wettability of polymers, many of which are hydrophobic. These methods include corona discharge, gas plasma exposure, flame treatment, and acid etching. All of these result in some level of surface oxidation. However, the wettability introduced by these processes degenerates after treatment, particularly when exposed to aqueous washing, elevated temperatures, or even simply storage in air.

SUMMARY OF THE INVENTION

This invention relates to a hydrophilic article for use in aqueous environments. The article includes a substrate, an ionic polymeric layer on the substrate, and a disordered polyelectrolyte coating which is ionically bonded to the ionic polymeric layer. The article, for example a contact lens, has a durable hydrophilic coating. Examples of aqueous environments are animal or plant fluids, water-based inks, treated or untreated water, and the media used in cell cultures and bioreactors.

The substrate may be selected from a range of geometries and materials. The substrate may have any texture, such as porous, nonporous, smooth, rough, even or uneven. The substrate supports an ionic polymeric layer.

The ionic polymeric layer on the substrate has ionic or ionizable groups on a polymer surface. These groups may or may not be in the bulk of the polymeric layer. Examples of ionic or ionizable groups are —$COO^-$, sulfate, and primary, secondary, or tertiary amines. The polymeric layer is a polymer or copolymer of thermoset, thermoplastic, biodegradable, and/or hydrophilic polymers. In the absence of ionic or ionized groups, the polymeric layer may be hydrophilic or hydrophobic.

The ionic polymeric layer is ionically bonded to a disordered, polyelectrolyte coating. There are neither linkages formed by use of a coupling agent nor covalent linkages between the polyelectrolyte coating and the ionic polymeric layer. Of course, Van der Waals forces and hydrogen bonds may or may not be present.

The polyelectrolyte coating includes one or more polyelectrolytes, which are generally high molecular weight polymers with multiple ionic or ionizable functional groups. At least one polyelectrolyte in the polyelectrolyte coating has a charge opposite to the overall charge of the ionic polymeric layer. The polyelectrolyte coating may also contain other elements, such as neutrally charged or bioactive molecules. Preferably, the coating forms a non-neutral complex, since the biocompatible, wettable, and wicking properties of the article are related, in part, to the presence of charged groups.

A disordered polyelectrolyte coating refers to (i) two or more polyelectrolytes that are intermixed, where the polyelectrolytes may be of the same or different charge; (ii) one or more polyelectrolytes that infiltrate the ionic polymeric layer where (a) at least one polyelectrolyte is of the same charge sign as the ionic groups associated with the ionic polymeric layer, and (b) there is some degree of chain entanglement; (iii) a polyelectrolyte intermixed with a non-polyelectrolyte additive, such as bioactive compounds such as heparin; and (iv) combinations of the above, including combinations with polyelectrolytes or non-polyelectrolytes that are not intermixed or that do not infiltrate the ionic polymeric layer, provided that the coating includes at least one infiltrating or intermixed polyelectrolyte.

Without intending to be bound, a polymer with short hydrophilic functional groups may seek a thermodynamic equilibrium, through the free rotation of the polymer backbone. Hydrophilic groups create a high-energy state and thus are gradually buried into the bulk of the material by rotational or diffusional migration. It is believed that multiple ionic anchors immobilize the polyelectrolyte backbone, which hinders molecular rotation and the subsequent loss of hydrophilicity. This phenomenon is a chain entanglement between the polyelectrolyte and the ionic polymeric layer. The disordered polyelectrolyate coating is ionically anchored, rather than physically adsorbed, onto the ionic polymeric layer, which may make the coating less susceptible to mechanical abrasion or hydrolytic decomposition.

One aspect of the present invention includes durable hydrophilic articles having a porous substrate. An example of such an article is the porous retaining matrix used in the immunoassay of an HCG pregnancy test kit. Other examples include a pH test strip, a bioreactor microcarrier, an implantable drug release device, and a filter. The polymeric layer is preferably polystyrene, polyester, polyethylene, polypropylene, polymethylmethacrylate, polyglycolic acid or polylactic acid, and the polyelectrolyte coating is preferably polyethyleneimine.

A drop of water placed on the disordered polyelectrolyte coating of a porous article is rapidly absorbed in less than 1 second after the article is exposed for 3 months to dry storage at 25° C. or aqueous storage at 50° C. Comparable stability is observed after 6 months or longer. In addition, a drop of water placed on a disordered polyelectrolyte coating of a porous article is absorbed in less than 2 seconds, and preferably less than 1 second, after 30 ultrasonic wash cycles. Hydrophilicity also remains high after 60 and 90 ultrasonic wash cycles.

Another aspect of the invention includes durable hydrophilic articles wherein the substrate is particulate. Examples of such articles include powders, beads, microcarriers, or tablets. The polymeric layer is preferably polystyrene, polyester, polyethylene, polypropylene, polymethylmethacrylate, polyglycolic acid or polylactic acid, and the polyelectrolyte coating is preferably polyethyleneimine. The substrate may or may not be porous. A powder having a disordered polyelectrolyte coating is wettable, and a drop of water added to an amount of such a powder will be absorbed, rather than form a bead.

A third aspect of the invention includes biomedical or biocompatible articles, where the initial advancing water contact angle of the disordered polyelectrolyte coating is less than 56°. Examples of ushc articles are intraocular lenses or other ophthalmic, prosthetic, or implantable articles or devices. Preferred materials for the polymeric layer include polyethylene, polypropylene, polyglycolic acid, polylactic acid, polyester, a polymer or copolymer of silicone, and a polymer or copolymer of poly-2-hydroxyethylmethacrylate, such as a copolymer of a silicone polymer and poly-2-hydroxylethyl-methacrylate. The polyelectrolyte coating is preferably polyethyleneimine.

In general, the initial advancing water contact angle of the disordered polyelectrolyte coating is smaller than the advancing water contact angle of the substrate before the coating is applied. The reduction is at least 20°, and may be greater than or equal to 30°, 50°, or even 70°. Thus, after the coating has been applied, the initial advancing water contact angle is, for example, less than 56° or less than 45° or 35°.

Before the coating is applied, a biomedical substrate preferably has an advancing water contact angle, for example, greater than 95°, 100°, or 110°. Such high water contact angles represent relatively low hydrophilicity or high hydrophobicity. After five and even fifteen ultrasonic washes, the disordered polyelectrolyte coating of the dried biomedical article has an advancing water contact angle less than 70°, and may be less than 60° or less than 45°. Even after exposure at 121°–125° C. for 15 or 30 minutes in an autoclave and cooling to room temperature, the advancing water contact angle of the coating is less than 60°. The coating is also resistant to extraction with organic solvents or detergents, as represented by an advancing water contact angle of less than 60° after extraction with methanol for 2 hours or even 18 hours. Other methods to measure hydrophilicity may be used to show resistance to environmental conditions or normal use.

The hydrophilicity or wettability of articles of the invention is resistant to one or more of the following: changes in pH, elevated temperatures, exposure to detergents or organic solvents, mechanical stress, abrasion, and repeated ultrasonic washings. Examples of articles of the invention which are suitable for long-term or multiple use applications include: hard and soft contact lenses, printing components, electrodes, bone replacement components, and in vitro retaining matrices for diagnostic test kits.

Other features and advantages of the present invention will be apparent from the following description of the preferred embodiments, and also from the appending claims.

DESCRIPTION OF THE PREFERRED EMBODIMENTS

This invention relates articles having a disordered polyelectrolyte coating ionically bonded to an ionic polymeric layer on a substrate. The polymeric layer can be on all areas of the substrate, or on selected areas. For example, a polymeric layer can be (i) a circular area having a smaller radius than the circular substrate it is on, (ii) a pair of parallel polymeric strips across a circular substrate, or (iii) any pattern of polymeric material on a substrate. For most embodiments, however, it is preferable that the polymeric layer is on most or all of the areas of the substrate.

Ionic groups can be on all areas of the polymeric layer, or on selected areas. For example, ionic groups can be (i) formed in a concentric increasing or decreasing gradient of surface charge density across a circular polymeric layer area, (ii) formed in a generally uniform surface charge density across one-half the area of the polymeric layer, or (iii) have different surface charge densities between the polymeric layer within a pore or channel and the polymeric layer on the outer surface of the article. In most embodiments, it is preferable for the ionic groups to be on all or most of the polymeric layer. Similarly, the disordered polyelectrolyte coating can be ionically bonded to all areas of the ionic polymeric layer, or to selected areas. It is preferable for the disordered polyelectrolyte coating to be ionically bonded to most or all areas of the ionic polymeric layer.

One aspect of the invention is an article made of a substrate that is a frame or grid, such as a polymeric or metal ring, with an empty center area. A polymeric membrane layer stretches across the hole and contacts the substrate along the perimeter or circumference of the ring substrate. The polymeric layer has two faces, one on each side of the ring. One or both faces of the polymeric membrane may have ionic groups. A disordered polyelectrolyte coating is ionically bonded to at least one face of the ionic polymeric membrane, forming at least one hydrophilic surface. Thus, this article may have a polyelectrolyyte coating on one or both sides of the ionic polymeric layer.

An article may have more than one such frame or grid. For example, an article may be a cube, wherein the twelve edges of the cube are the substrate. The six square sides of the cube are the ionic polymeric layer, wherein each of the six, square ionic polymeric membranes has an inner face and an outer face. The disordered polyelectrolyte coating can be ionically bound (i) to the outer (or inner) faces of six sides, (ii) to the outer faces of five sides and to the inner face of the sixth side, or (iii) in any manner to direct the passage or diffusion of an aqueous solution through the cube.

Another article of the invention has an ionic polymeric hydrogel layer ionicallly bonded to a disordered polyelectrolyte coating containing only one polyelectrolyte, such as polyethyleneimine. A hydrogel polymer may be a copolymer of silicone polymers and poly-2-hydroxyethylmethacrylate. An example of such an article is an oxygen-permeable contact lens with a high D/K value. Another article of the invention has an ionic polymeric layer ionically bonded to a disordered polyelectrolyte coating containing two polyelectrolytes of opposite charges.

A substrate may be made of any material, provided that a polymeric surface may be bonded to at least some area of the substrate. The substrate may be made of metal, ceramic, glass, composite or a polymer, which may be the same or different polymer as the polymeric layer discussed below, and may or may not be porous. An example of an article which has a substrate and a polymeric layer of the same material is a fabric made of polypropylene.

A porous substrate has (i) a surface with one or more pores, for example, of an average diameter between 0.01 microns and 1 mm, (ii) an uneven or undulating, non-flat surface, such as a woven, non-woven, compressed, perforated, or etched material, or (iii) a combination of (i) and (ii). A pore may also be considerably larger than 1 mm, and need not penetrate from one surface of the substrate completely through the other side. A hydrophilic article of the invention having a substrate with pores of a diameter around 50 microns or larger, such as 200 to 500 microns, will tend to have no measurable water contact angle; it will completely wet out ("cwo") when one or more water drops are applied to the coating surface. Rather than beading, water drops are rapidly absorbed or wicked into the hydrophilic surface material. Examples of a porous articles include nonwoven and woven fabrics, retaining matrices, porous membranes, sheets, or films.

Porous articles can be retaining matrices or chromatographic matrices used in sample preparation/filtration, reagent immobilization, and reagent delivery. An example of a retaining matrix used in sample preparation is a filter to retain solids or cells, while allowing liquids such as cell extracts to pass through. In addition, a retaining matrix may contain an immobilized reagent, such as an antibody. Such an article is suitable for systems in which a target component in a liquid test sample contacts and is selectively bound to the immobilized reagent. Meanwhile, the liquid sample as a whole continues to move through the retaining matrix. This can be considered a form of chromatography since the target component is separated from the test sample. In a third example, the retaining matrix contains a dry reagent, such as an indicator or enzyme. As a sample such as blood or urine wets and spreads throughout the porous retaining matrix, the retained reagent is dissolved and released into the liquid sample.

Porous matrices are suitable for reagent immobilization for several reasons, including (i) large surface area to volume ratio, (ii) greater reagent (e.g., protein) binding capacity, and (iii) superior continuous passage of a liquid either laterally or in a direction perpendicular to the plane of a membrane or other matrix. Retaining matrices are used for diagnostic and research purposes. Examples include the matrices in pH test strips, ELISA assays, glucose test strips, and HCG pregnancy dip sticks.

A particulate substrate refers to particles having a largest average dimension between 1 micron and 3 cm. Particulates may be porous or non-porous, and may be spherical, oblong, cylindrical, granular, or of other shapes, irregular, or regular. Examples of particulate substrates include powders, disks, rods, tablets, and beads. Hydrophilic articles having particulate substrates include retaining matrices (see above for general discusion), controlled drug release particles, wettable powders, and bioreactor microcarriers.

A biomedical substrate refers, in part, to the fields of medicine, and the study of living cells and systems. These fields include diagnostic, therapeutic, and experimental human medicine, veterinary medicine, and agriculture. Examples of medical fields include ophthalmology, orthopedics and prosthetics, immunology, dermatology, pharmacology, and surgery; nonlimiting examples of research fields include cell biology, microbiology, and chemistry. The term "biomedical" also relates to chemicals and compositions of chemicals, regardless of their source, that (i) mediate a biological response in vivo, (ii) are active in an in vitro assay or other model, e.g., an immunological or pharmacological assay, or (iii) can be found within a cell or organism. The term "biomedical" also refers to the separation sciences, such as those involving processes of chromatography, osmosis, reverse osmosis, and filtration.

Examples of biomedical articles include research tools, industrial, and consumer applications. Biomedical articles include separation articles, implantable articles, and ophthalmic articles. Ophthalmic articles include soft and hard contact lenses, intraocular lenses, and forceps, retractors, or other surgical tools that contact the eye or surrounding tissue. A preferred biomedical article is a soft contact lens made of a silicon-containing hydrogel polymer that is highly permeable to oxygen. Separation articles include filters, osmosis and reverse osmosis membranes, and dialysis membranes, as well as biosurfaces such as artificial skins or other membranes. Implantable articles include catheters, and segments of artificial bone, joints, or cartilage. An article may be in more than one category, for example, an artificial skin is a porous, biomedical article.

Examples of cell culture articles are glass beakers, plastic petri dishes, and other implements used in tissue culture or cell culture processes. A preferred example of a cell culture article is a bioreactor microcarrier, a silicone polymer matrix used in immobilized cell bioreactors, where the geometry, porosity, and density of the particulate microcarrier may be controlled to optimize performance. Ideally, the microcarrier is resistant to chemical or biological degradation, to high impact stress, to mechanical stress (stirring), and to repeated steam or chemical sterilization. In addition to silicone polymers, other materials may also be suitable.

This invention may also be applied in the food industry, the paper printing industry, hospital supplies, diapers and other liners, and other areas where hydrophilic, wettable, or wicking articles are desired.

An article of the invention has an ionic polymeric layer on the substrate. The polymeric layer may be a homopolymer or copolymer of thermoset, thermoplastic, ionizable, and hydrophilic polymers. Examples include (A) polyethylene, polypropylene, polystyrene, polyester, polycarbonates, silicone polymers, polyurethane, polyamides, polyimides, polyalkylacrylates, polyalkylmethacrylates, and fluorocarbon polymers; (B) poly-2-hydroxylethylmethacrylates, polyhydroxyalkyl methacrylates, polyhydroxylalkyl acrylates, polyacrylic amides, polymethacrylic amides, polyvinyl alcohols, polyethylene oxide, and polyvinyl pyrrolidone; (C) polylactic acid, polyglycolic acid, polyglycolide-co-lactides, polydioxanones, poly(glycolide-co-trimethylene carbonates), polyethylene carbonates, polyiminocarbonates, poly-$\beta$-hydroxybutyrates, polyesteramides, polyorthoesters, polyanhydrides, and cyanoacrylates; and (D) copolymers of members of (A), (B) and (C). The polymers of group (D) include copolymer combinations of members from groups such as (A) and (B); (B) and (C); (A) and (C); (A) and (A); and (A) and (B) and (C). The polymeric layer is preferably selected from polyester, polypropylene, polystyrene, polymethylmethacrylate, polyethylene, polyglycolic acid, and polylactic acid. A polymeric layer can be made of one or more polymers. Preferably, the polymeric layer comprises or consists essentially of one or more polymers, the balance consisting of up to 10% by weight of additives known in the art, such as one or more polymer crosslinking agents, or impurities.

An ionic polymeric layer can be obtained by several methods known in the art. Ionic groups may result from a treatment of the polymeric layer, such as plasma discharge or acid/base chemical modification, or ionic or ionizable groups may have been incorporated into the bulk material of the polymeric layer itself. The sign of the individual ionic groups and the overall charge of the ionic polymeric layer may each be positive or negative. For example, a polymer such as polyethylene may oxidized by glow discharge plasma, electron beam treatment, corona discharge, and X-ray treatment, to create an ionic surface on the polymeric layer. See e.g., Horbett et al., U.S. Pat. No. 4,919,659. One advantage of plasma treatments is the production of more than one kind of ionic group on the polymeric surface.

As an example, an anionic polymeric layer can be created by plasma treatments of oxidizing gases such as oxygen, carbon dioxide, carbon monoxide, and sulfur dioxide. These oxidizing gases may be used separately, in combination with each other, or in combination with an inert gas. Cationic polymeric layers may be created by low pressure gas plasma treatments with ammonia, allylamine, or mixtures of nitrogen and hydrogen. These gases may also be used separately, in combination with each other, or in combination with an inert gas. See also , e.g., Peyman et al., U.S. Pat. No. 4,312,575. In addition, a monomer such as an acrylate, methacrylate, or vinyl sulfonate may be incorporated into the polymeric layer formulation. See, e.g., Ellis et al., U.S. Pat. No. 4,168,112. Treatment with aqueous acid or base can also produce an ionic polymeric layer. The surface charge density should be preferably greater than 10%, e.g., 20%, 30% or 50%, although lower surface charge densities may be appropriate for some applications.

Polyelectrolytes can be linear, branched, or crosslinked polymers or copolymers. Examples include polyethyleneimine, polyionenes, polyaminoalkyl methacrylate, polyvinylpyridine, polylysine, polyacrylic acid, polymethacrylic acid, polysulfonic acid, polyvinyl sulfate, polyacrylamido-2-methyl-1-propanesulfonic acid, and polystyrene sulfonic acid. Preferred polyelectrolytes include polyethyleneimine and polyacrylamido-2-methyl-1- propanesulfonic acid. Ionic or ionizable groups may be present in every repeat unit, or only in some repeat units. The molecular weight of polyelectrolytes should be between 5,000 Daltons and one million Daltons, with higher molecular weights, for example, between 75,000 and 200,000 Daltons being preferred, to enhance the stability of the coating through increased chain entanglement or numbers of anchors.

As an example, a substrate with an anionic polymeric layer can be dip-coated with a polycationic solution, then dried in air or with a heat source. The polyelectrolyte solution contains, in this case, one or more positively charged polyelectrolytes, and preferably has a pH between 5 and 10. Preferably, the solution is at room temperature, but it can also be at lower or higher temperatures, as easily determined by those skilled in the art. The soaking period is between a few seconds and a few hours, and is preferably 20–30 minutes. Other methods of application include spray, wash, vapor deposition, brush, roller, and other methods known in the art. In addition, a cationic polymeric layer may be obtained and similarly coated with solution containing a polyanion.

This method is suitable for coating a variety of physical forms, including films, sheets, rods, tubes, molded parts (regular or irregular shapes), fibers, fabrics, and particulates. Ionic polymeric layers which are smooth or rough, flat or curved, solid or porous may be coated.

After drying, the substrate may be dip-coated with one or more additional polyelectrolyte or other solutions. An additional solution may contain polyelectrolytes of the same or different charge sign. Additional polyelectrolyte dip-coat steps may be desirable for some applications to produce a disordered coating of some complexity. For example, a complex disordered polyelectrolyte coating may include non-discrete layers of varying or alternating charges; varying or alternating surface coating densities; varying or alternating surface charge densities; and varying degrees of intermixing. The charge and thickness of the coating may be controlled by altering polyelectrolyte concentration, soaking time, pH, and number of dip-coat steps. To the extent that a thickness of a disordered coating can be measured, the coating should be between 5 and 2500 Angstroms, preferably 20–500 Angstroms. The coating may contain other polyelectrolytes of the same or opposite charge; other non-polyelectrolyte charged or ionizable additives; or charge-neutral additives that enhance biocompatibility or that are bioactive. These other polyelectrolytes and additives may be included in a polyelectrolyte solution, or may be applied before or after a dip-coat in another manner. Where a polyelectrolyte coating comprises polyethyleneimine, one or more additional polyelectrolytes or other additives can be present in equal or unequal proportions.

Polyelectrolyte solutions should be between 0.001% and 10% (w/v), and preferably between 1% and 5%, such as 3%. Higher concentrations may be suitable, but may also result in non-uniform coatings and longer drying times. Aqueous solutions of polyelectrolytes can have a pH between 4 to 10. Suitable solvents include alcohols, e.g., straight chain or branched or aromatic alcohols, and polyols such as glycol and ethylene glycol, or aqueous solutions thereof. Organic solvents such as chloroform and dimethylformamide may also be desirable for polymers such as polyethylene. One skilled in the art will easily be able to determine what solvent conditions are appropriate for a particular polymeric layer.

In one aspect of the invention, where the polymeric layer is a hydrogel polymer or copolymer, the solvent system can be chosen to cause the polymeric layer to absorb some of the solvent and swell. Swelling the polymeric layer allows one or more polyelectrolytes to penetrate or infiltrate the polymeric layer. As discussed above, such infiltration is believed to enhance the durability or permanence of the hydrophilic coating.

The durability of the hydrophilic coating can be determined by several methods including measuring water contact angles (see Examples section). Advancing and receding water contact angles of the disordered polyelectrolyte coating of the invention are measured by methods well known in the art, such as a computer-video processed goniometer. A sessile drop of deionized water is dispensed and its image is displayed on a computer monitor. The advancing or receding water contact angle of the water drop is then determined by computer software. An initial advancing water contact angle is the advancing water contact angle which is measured soon after the last intended polyelectrolyte or other solution is applied and dried. An advancing water contact angle of a substrate is measured before a polyelectrolyte coating is applied, and before the ionizing treatment, e.g., plasma discharge, if any. An advancing water contact angle of an ionic polymeric layer is measured after the ionizing treatment, if any, but before a polyelectrolyte coating is applied. The coatings of the present invention cause a reduction of at least 20°, and preferably 30° or 40°, in the advancing water contact angle, compared with the advancing water contact angle of the substrate.

In wicking or hydrophilicity determinations, rapid absorption is generally less than 5 seconds, preferably less than 2 seconds, and more preferably less than 1 second or a fraction thereof, such as one-sixth of a second. Storage periods are generally more than 1 month, such as 3 months, 6 months, 9 months or 1 year, or longer. Some of the coatings are non-leaching, non-toxic, and noncytotoxic according to USP XXII test methods.

Without further elaboration, it is believed that one skilled in the art can, based on the description herein, utilize the present invention to its fullest extent. The following specific embodiments are, therefore, to be construed as merely illustrative, and not limitative of the remainder of the disclosure in any way. All publications herein are incorporated by reference.

EXAMPLE 1

Carbon-filled porous polyethylene was treated in an $O_2$ plasma for 3 minutes at 30 mTorr pressure, 50 watts power at 13.56 MHz. The treated sample was subsequently placed into a 3% aqueous solution of polyethyleneimine (PEI) (Polymin SNA, BASF Corp.). The solution was placed under vacuum for 5 minutes to remove the trapped air from the porous substrate. The sample was then soaked in the PEI solution for 20 minutes and removed for drying in air. The wettability of the coated sample was then determined using contact angle measurements. The coated surface exhibited complete wettability while the untreated sample showed a high water contact angle of 112°. Water drops were absorbed immediately into the coated polyethylene.

EXAMPLE 2

The stability of the hydrophilic coating of the invention has been examined in aqueous and dry storage at both room temperature and 50° C. After various storage times, the samples were removed from the storage environments, rinsed with water and vacuum dried prior to wettability analysis. Table I shows the time it took for water drops to be completed absorbed by the coated material. The time measurement mechanism was accurate to one-sixth of a second, thus a 0-second entry represents less than one-sixth of a second. In a 6 month stability study, the results indicated that a stable hydrophilic coating was obtained on carbon-filled porous polyethylene.

TABLE I

Stability of the coating on treated carbon filled porous PE

| Storage Time (Days) | Time for water droplet to be completely absorbed by the coated carbon-filled polyethylene (Seconds) | | | |
|---|---|---|---|---|
| | Dry Storage in Air | | Wet Storage in Water | |
| | Room Temp. | 50° C. | Room Temp. | 50° C. |
| 0 | 0 | 0 | 0 | 0 |
| 1 | 0 | 0 | 0 | 0 |
| 2 | 0 | 0 | 0 | 0 |
| 5 | 0 | 0 | 0 | 0 |
| 6 | 0 | 0 | 0 | 0 |
| 7 | 0 | 0 | 0 | 0 |
| 8 | 0 | 0 | 0 | 0 |
| 9 | 0 | 0 | 0 | 0 |
| 13 | 2 | 0 | 0 | 0 |
| 14 | 0 | 0 | 2 | 0 |
| 15 | 0 | 0 | 0 | 0 |
| 16 | 0 | 0 | 0 | 0 |
| 19 | 0 | 0 | 2 | 0 |
| 21 | 0 | 0 | 2 | 0 |
| 22 | 0 | 0 | 2 | 0 |
| 26 | 0 | 0 | 2 | 0 |
| 27 | 0 | 0 | 2 | 0 |
| 28 | 0 | 0 | 0 | 0 |
| 29 | 0 | 0 | 0 | 0 |
| 30 | 0 | 0 | 0 | 0 |
| 40 | 0 | 0 | 0 | 0 |
| 44 | 0 | 0 | 1 | 0 |
| 50 | 0 | 0 | 0 | 0 |
| 61 | 0 | 0 | 0 | 0 |
| 65 | 0 | 0 | 1 | 0 |
| 78 | 0 | 0 | 0 | 0 |
| 86 | 0 | 0 | 0 | 0 |
| 97 | 0 | 0 | 0 | 0 |
| 106 | 0 | 0 | 0 | 0 |
| 113 | 0 | 0 | 0 | 0 |
| 121 | 0 | 0 | 0 | 0 |
| 135 | 0 | 0 | 0 | 0 |
| 194 | 0 | 0 | 0 | 0 |

EXAMPLE 3

Durability of the coating on the carbon filled polyethylene has also been examined using repeated ultrasonic washing in water. Coated samples were first immersed in water under vacuum for 5 minutes, then ultrasonically rinsed in water for three 10 min. cycles, and vacuum dried prior to wettability analysis. Table II shows the durability of the coating in repeated ultrasonic washing in water. The results indicated that the coating developed in this invention was durable over 100 repeated washing cycles.

TABLE II

Durability of the coating on porous polyethylene

| Days After Coating | Time for water droplet to be completely absorbed by polyethylene (Seconds) | Total No. of Ultrasonic Washing Cycles |
|---|---|---|
| 0 | 0 | 3 |
| 1 | 0 | 6 |
| 2 | 0 | 9 |
| 3 | 0 | 12 |
| 6 | 0 | 15 |
| 7 | 0 | 18 |
| 8 | 0 | 21 |
| 10 | 0 | 24 |
| 14 | 0 | 27 |
| 15 | 0 | 30 |
| 16 | 0 | 33 |
| 17 | 0 | 36 |
| 20 | 0 | 39 |
| 21 | 0 | 42 |
| 23 | 0 | 45 |
| 24 | 0 | 48 |
| 28 | 0 | 51 |
| 29 | 0 | 54 |
| 30 | 0 | 57 |
| 34 | 0 | 60 |
| 37 | 0 | 63 |
| 38 | 0 | 66 |
| 41 | 0 | 69 |
| 42 | 0 | 72 |
| 44 | 0 | 75 |
| 45 | 0 | 78 |
| 48 | 0 | 81 |
| 49 | 0 | 84 |
| 57 | 0 | 87 |
| 58 | 0 | 90 |
| 62 | 1 | 93 |
| 63 | 1 | 96 |
| 64 | 1 | 99 |
| 65 | 0 | 102 |
| 71 | 12 | 105 |
| 75 | 65 | 108 |

EXAMPLE 4

Porous polyethylene sheets were treated with $O_2$ plasma for 30 minutes at 250 watts and 60 mTorr. The treated polyethylene was subsequently placed into a 3% aqueous solution of polyethyleneimine (PEI) (Polymin SNA, BASF Corp.) under vacuum for 5 minutes. The sample was then soaked in the PEI solution for 20 minutes and removed for drying in air. The wettability of the coated sample was then analyzed using contact angle measurements. The coated surface exhibited complete wettability while the untreated sample showed a high water contact angle of 109°. Complete and rapid absorption of the water droplet into the coated material was observed.

EXAMPLE 5

Durability of the material obtained in Example 4 was tested. Table III lists the contact angle results for the treated polyethylene sheets. The results demonstrated that a tenaciously hydrophilic coating was obtained.

TABLE III

Wettability of hydrophilic treated porous polyethylene

| Sample | Dry Storage After Coating at Room Temp. | | | | |
|---|---|---|---|---|---|
| | 0 day | 7 days | 14 days | 30 days | 122 days |
| $O_2$ plasma treated/ PEI coated | 0° | 0° | 0° | 0° | 0° |

EXAMPLE 6

Hard contact lenses containing silicone polymers were treated in a $CO_2$ plasma for 15 minutes on each side at 50 mTorr, 80 watts at 13.56 MHz. A 1% PEI solution (Polymin Waterfree, BASF Corp.) was prepared in water and adjusted to pH 7.0 by adding HCl. The samples were soaked in a PEI solution for 10 minutes at room temperature and subsequently rinsed with water to remove excess PEI.

EXAMPLE 7

The samples obtained in Example 6 were further rinsed with phosphate buffered saline prior to autoclave sterilization. The sterilization was performed at 121° C. for 30 min. The contact angles for treated lenses are listed in Table IV. The reduced contact angles revealed that the coated lenses became hydrophilic. In addition, the hydrophilic coating remained stable even after autoclave sterilization. The hydrophilic-treated contact lenses had an advancing water contact angle of 51°±4 and a receding water contact angle of 38°±5.

EXAMPLE 8

Dry hydrogel contact lenses containing silicone polymer are hydrophobic. To improve surface wettability, such lenses were first treated in $CO_2$ plasma for 10 minutes on each side at 50 mTorr pressure, 100 watts power at 13.56 MHz. The lenses were then placed into a 1% aqueous solution of PEI (Polymin, Waterfree, BASF Corp.) and allowed to soak for 20 minutes at room temperature. After soaking, the samples were rinsed in water 5 times and dried in air.

EXAMPLE 9

Water contact angle measurements were used to determine surface wettability of the treated contact lenses in Example 8. Stability of the hydrophilic coatings was evaluated under repeated washing, solvent extraction and autoclaving conditions. In each washing cycle, the samples were rinsed ultrasonically in fresh water for 10 minutes. Extraction of the treated samples was carried out in methanol for 18 hours. Autoclaving conditions were 121°–125° C. for 30 minutes. Table V lists the water contact angles for the treated contact lenses. The results shown in Table V indicate that a significant reduction in water contact angles was observed on the treated lenses prepared according to the invention. Lenses treated with this invention, on the other hand, exhibited only a small decrease in wettability initially and resistant to long term repeated washing. In addition, the coated lenses remained hydrophilic after extraction in methanol and exposure to autoclave conditions.

TABLE IV

Water contact angles for the coated hydrogel lenses

| Sample | $CO_2$/PEI | | Plasma Treated | $O_2$ Plasma Treated | |
|---|---|---|---|---|---|
| | Advancing | Receding | Advancing | Receding | |
| Treated | 24° ± 1 | 17° ± 1 | 29° ± 1 | 20° ± 1 | |
| Treated/ Washed 5 cycles | 67° ± 2 | 21° ± 1 | 96° ± 1 | 35° ± 1 | |
| Treated/ Washed 15 cycles | 67° ± 3 | 24° ± 1 | 115° ± 1 | 39° ± 1 | |
| Treated/Extracted | 50° ± 1 | 32° ± 1 | 115° ± 1 | 40° ± 1 | |
| Treated/Autoclaved | 30° ± 4 | 9° ± 1 | 112° ± 1 | 38° ± 1 | |

EXAMPLE 10

Non-woven polyester and polypropylene fabrics were treated in a $CO_2$ plasma for 20 minutes at 50 m Torr, 100 watts power at 13.56 MHZ. The fabrics were then soaked in a solution of PEI (Polymin, SNA, BASF Corp.) at room temperature for 20 minutes, then dried overnight.

EXAMPLE 11

The wettability of the samples obtained Example 10 was examined using water contact angle measurements, shown in Table IV. After overnight drying, the samples were washed ultrasonically in water 3 times for 10 minutes each. The results indicated that fabric surfaces treated with this invention were durably hydrophilic.

TABLE V

Wettability of treated non-woven fabrics

| Sample | Before Washing | After Washing |
|---|---|---|
| polyester | cwo | cwo |
| polypropylene | cwo | cwo |

EXAMPLE 12

Biodegradable polymer powders containing polyglycolic acid (PGA) and polyactic acid (PLA) (200 μm) are hydrophobic when dry. Such polymer powders cannot mix with water. Fifty gram of the polymer powders were placed in a rotating reactor and treated with an acrylic acid plasma at 100 mTorr, 50 watts for 30 minutes. After treatment, a PEI solution in IPA (0.5 g/75 ml) was added to the treated powders. The solvent was then removed by vacuum evaporation. The coated PGA-PLA powders became wettable. For example, water was absorbed, rather than beading on the surface of a sample of powder.

Other Embodiments

From the above description, one skilled in the art can easily ascertain the essential characteristics of the present invention, and without departing form the spirit and scope thereof, can make various changes and modifications of the invention to adapt it to various usages and conditions. Thus, other embodiments are also within the claims.

What is claimed is:

We claim:

1. A hydrophilic article for use in aqueous environments, comprising a porous substrate;

an ionic polymeric layer on said substrate; and a disordered polyelectrolyte coating ionically bonded to said polymeric layer;

wherein said porous substrate has a surface with pores of an average diameter between 0.01 microns and 1 mm, or is made of perforated material.

2. The article of claim 1, wherein a drop of water placed on said coating is absorbed in less than 1 second after said article is subjected to dry storage at 25° C. for 3 months.

3. The hydrophilic article of claim 2, wherein said polymeric layer comprises a polymer selected from the group consisting of (A) polyethylene, polypropylene, polystyrene, polyester, polycarbonates, silicone polymers, polyurethane, polyamides, polyimides, polyalkylacrylates, polyalkylmethacrylates, and fluorocarbon polymers; (B) poly-2-hydroxylethylmethacrylate, polyhydroxylalkyl methacrylates, polyhydroxylalkyl acrylates, polyacrylic amides, polymethacrylic amides, polyvinyl alcohols, polyethylene oxide, and polyvinyl pyrrolidone; (C) polylactic acid, polyglycolic acid, polyglycolide-co-lactides, polydioxanones, poly (glycolide-co-trimethylene carbonates), polyethylene carbonates, polyiminocarbonates, poly-β-hydroxybutyrates, polyesteramides, polyorthoesters, polyanhydrides, and cyanoacrylates; and (D) copolymers of members of (A), (B) and (C); and said polyelectrolyte coating comprises a polyelectrolyte selected from the group consisting of polyethyleneimine, polyaminoalkyl methacrylate, polyvinylpyridine, polylysine, polyacrylic acid, polymethacrylic acid, polysulfonic acid, polyvinyl sulfate, polyacrylamido-2-methyl-1-propanesulfonic acid, and polystyrene sulfonic acid.

4. The article of claim 3, wherein said article is a matrix which retains solids, cells, or a target component.

5. The article of claim 1, wherein a drop of water placed on said coating is absorbed in less than 1 second after said article is subjected to aqueous storage at 50° C. for 3 months and dried.

6. The article of claim 5, wherein said polymeric layer comprises a polymer selected from the group consisting of (A) polyethylene, polypropylene, polystyrene, polyester, polycarbonates, silicone polymers, polyurethane, polyamides, polyimides, polyalkylacrylates, polyalkylmethacrylates, and fluorocarbon polymers; (B) poly-2-hydroxylethylmethacrylate, polyhydroxylalkyl methacrylates, polyhydroxylalkyl acrylates, polyacrylic amides, polymethacrylic amides, polyvinyl alcohols, polyethylene oxide, and polyvinyl pyrrolidone; (C) polylactic acid, polyglycolic acid, polyglycolide-co-lactides, polydioxanones, poly (glycolide-co-trimethylene carbonates), polyethylene carbonates, polyiminocarbonates, poly-β-hydroxybutyrates, polyesteramides, polyorthoesters, polyanhydrides, and cyanoacrylates; and (D) copolymers of members of (A), (B) and (C); and said polyelectrolyte coating comprises a polyelectrolyte selected from the group consisting of polyethyleneimine, polyaminoalkyl methacrylate, polyvinylpyridine, polylysine, polyacrylic acid, polymethacrylic acid, polysulfonic acid, polyvinyl sulfate, polyacrylamido-2-methyl-1-propanesulfonic acid, and polystyrene sulfonic acid.

7. The article of claim 6, wherein said article is a microcarrier for cultering cells.

8. The article of claim 1, wherein a drop of water placed on said coating is absorbed in less than 1 second after 30 ultrasonic wash cycles with deionized water.

9. The article of claim 1, wherein a drop of water placed on said coating is absorbed in less than 2 seconds after 60 ultrasonic wash cycles with deionized water.

10. The article of claim 8, wherein said polymeric layer comprises a polymer selected from the group consisting of (A) polyethylene, polypropylene, polystyrene, polyester, polycarbonates, silicone polymers, polyurethane, polyamides, polyimides, polyalkylacrylates, polyalkylmethacrylates, and fluorocarbon polymers; (B) poly-2-hydroxylethylmethacrylate, polyhydroxylalkyl methacrylates, polyhydroxylalkyl acrylates, polyacrylic amides, polymethacrylic amides, polyvinyl alcohols, polyethylene oxide, and polyvinyl pyrrolidone; (C) polylactic acid, polyglycolic acid, polyglycolide-co-lactides, polydioxanones, poly (glycolide-co-trimethylene carbonates), polyethylene carbonates, polyiminocarbonates, poly-β-hydroxybutyrates, polyesteramides, polyorthoesters, polyanhydrides, and cyanoacrylates; and (D) copolymers of members of (A), (B) and (C); and said polyelectrolyte coating comprises a polyelectrolyte selected from the group consisting of polyethyleneimine, polyaminoalkyl methacrylate, polyvinylpyridine, polylysine, polyacrylic acid, polymethacrylic acid, polysulfonic acid, polyvinyl sulfate, polyacrylamido-2-methyl-1-propanesulfonic acid, and polystyrene sulfonic acid.

11. The article of claim 1, wherein said polymeric layer comprises a polymer selected from the group consisting of (A) polyethylene, polypropylene, polystyrene, polyester, polycarbonates, silicone polymers, polyurethane, polyamides, polyimides, polyalkylacrylates, polyalkylmethacrylates, and fluorocarbon polymers; (B) poly-2-hydroxylethylmethacrylate, polyhydroxylalkyl methacrylates, polyhydroxylalkyl acrylates, polyacrylic amides, polymethacrylic amides, polyvinyl alcohols, polyethylene oxide, and polyvinyl pyrrolidone; (C) polylactic acid, polyglycolic acid, polyglycolide-co-lactides, polydioxanones, poly (glycolide-co-trimethylene carbonates), polyethylene carbonates, polyiminocarbonates, poly-β-hydroxybutyrates, polyesteramides, polyorthoesters, polyanhydrides, and cyanoacrylates; and (D) copolymers of members of (A), (B) and (C); and said polyelectrolyte coating comprises a polyelectrolyte selected from the group consisting of polyethyleneimine, polyaminoalkyl methacrylate, polyvinylpyridine, polylysine, polyacrylic acid, polymethacrylic acid, polysulfonic acid, polyvinyl sulfate, polyacrylamido-2-methyl-1-propanesulfonic acid, and polystyrene sulfonic acid.

12. The article of claim 11, wherein said polymeric layer is selected from polyester, polypropylene, polyethylene, polystyrene, polymethylmethacrylate, polyglycolic acid, and polylactic acid; and said polyelectrolyte coating comprises polyethyleneimine.

13. The article of claim 1, wherein said article is a matrix which retains solids, cells, or a target component.

14. The article of claim 1, wherein said article is a microcarrier for culturing cells.

* * * * *